(12) United States Patent
Bowran et al.

(10) Patent No.: US 7,829,762 B2
(45) Date of Patent: Nov. 9, 2010

(54) WHEAT PLANTS HAVING INCREASED RESISTANCE TO IMIDAZOLINONE HERBICIDES

(75) Inventors: David Bowran, Sawyers Valley (AU); Iain Barclay, Shelley (AU); Kevin F. Jose, Greenwood (AU)

(73) Assignee: Department of Agriculture, South Perth (AU)

( * ) Notice: Subject to any disclaimer, the term of this patent is extended or adjusted under 35 U.S.C. 154(b) by 479 days.

(21) Appl. No.: 10/520,738

(22) PCT Filed: Jul. 9, 2003

(86) PCT No.: PCT/IB03/04645

§ 371 (c)(1),
(2), (4) Date: Sep. 19, 2005

(87) PCT Pub. No.: WO2004/016073

PCT Pub. Date: Feb. 26, 2004

(65) Prior Publication Data

US 2006/0095992 A1 May 4, 2006

Related U.S. Application Data

(60) Provisional application No. 60/394,991, filed on Jul. 10, 2002.

(51) Int. Cl.
*A01H 5/00* (2006.01)
*A01H 5/10* (2006.01)
(52) U.S. Cl. ............ 800/300; 800/260; 800/320.3
(58) Field of Classification Search .............. None
See application file for complete search history.

(56) References Cited

U.S. PATENT DOCUMENTS

| | | | |
|---|---|---|---|
| 4,761,373 A | 8/1988 | Anderson et al. | |
| 5,013,659 A | 5/1991 | Bedbrook et al. | |
| 5,304,732 A | 4/1994 | Anderson et al. | |
| 5,331,107 A | 7/1994 | Anderson et al. | |
| 5,731,180 A | 3/1998 | Dietrich | |
| 5,767,361 A | 6/1998 | Dietrich | |
| 5,853,973 A | 12/1998 | Kakefuda et al. | |
| 5,928,937 A | 7/1999 | Kakefuda et al. | |
| 6,211,438 B1 | 4/2001 | Anderson et al. | |
| 6,211,439 B1 | 4/2001 | Anderson et al. | |
| 6,222,100 B1 | 4/2001 | Anderson et al. | |
| 6,225,105 B1 | 5/2001 | Sathasivan et al. | |
| 2004/0237134 A1* | 11/2004 | Pozniak et al. | 800/278 |
| 2004/0244080 A1 | 12/2004 | Hucl | |
| 2005/0044597 A1 | 2/2005 | Konzak | |

FOREIGN PATENT DOCUMENTS

| | | |
|---|---|---|
| EP | 0 360 750 A2 | 3/1990 |
| EP | 0 375 875 | 7/1990 |
| EP | 0 525 384 A2 | 2/1993 |
| EP | 0 508 161 B1 | 5/2000 |
| WO | WO 90/14000 A1 | 11/1990 |
| WO | WO 00/53763 | 9/2000 |
| WO | WO 02/092820 A1 | 11/2002 |
| WO | WO 03/013225 A2 | 2/2003 |
| WO | WO 03/014356 A1 | 2/2003 |
| WO | WO 03/014357 A1 | 2/2003 |

OTHER PUBLICATIONS

Newhouse, K., et al., "Tolerance to Imidazolinone Herbicides in Wheat," *Plant Physiol.*, 1992, pp. 882-886, vol. 100.
GenBank Accession No. BE417248.
GenBank Accession No. BF200418.
Shaner, D., et al., "Imidazolinone-Resistant Crops: Selection, Characterization and Management," *Herbicide-Resistant Crops: Agricultural, Environmental, Economic, Regulatory, and Technical Aspects*, 1996, pp. 144-157, Lewis Publishers.
J. Andrew Kendig and M.S. DeFelice, "ALS Resistance Cocklebur (Xanthium strumarium L.) in Missouri", *WSSA Abstracts*, vol. 34, Feb. 7-10, 1994, 1994 Meeting of the Weed Science Society of America.
Barrett, M., "Protection of Grass Crops from Sulfonylurea and Imidazolinone Toxicity," *Crop Safeners for Herbicides*, 1989, pp. 195-220, Academic Press, Inc.
Bernasconi, P., et al., "A Naturally Occurring Point Mutation Confers Broad Range Tolerance to Herbicides That Target Acetolactate Synthase," *The Journal of Biological Chemistry*, 1995, pp. 17381-17385, vol. 270(29).
Brown, M., et al., "Hydrolytic Activation versus Oxidative Degradation of Assert Herbicide, an Imidazolinone Aryl-carboxylate, in Susceptible Wild Oat versus Tolerant Corn and Wheat," *Pesticide Biochemistry and Physiology*, 1987, pp. 24-29, vol. 27, Academic Press, Inc.
Chang, A., and R. Duggelby, "Herbicide-resistant Forms of *Arabidopsis thaliana* Acetohydroxyacid Synthase: Characterization of the Catalytic Properties and Sensitivity to Inhibitors of Four Defined Mutants," *Biochemistry J.*, 1998, pp. 765-777, vol. 333.
Chong C., and J. Choi, "Amino Acid Residues Conferring Herbicide Tolerance in Tobacco Acetolactate Synthase," *Biochemical and Biophysical Research Communications*, 2000, pp. 462-467, vol. 279, Academic Press.
Duggleby, R., et al., "Systematic Characterization of Mutations in Yeast Acetohydroxyacid Synthase," *Eur. J. Biochem.*, 2003, pp. 2895-2904, vol. 270.
Hattori, J., et al., "Multiple Resistance to Sulfonylureas and Imidazolinones Conferred by an Acetohydroxyacid Synthase Gene with Separate Mutations for Selective Resistance," *Molecular Genetics*, 1992, pp. 167-173, vol. 232.
Lee, Y., et al., "Effect of Mutagenesis at Serine 653 of *Arabidopsis thaliana* Acetohydroxyacid Synthase on the Sensitivity to Imidazolinone and Sulfonylurea Herbicides," *FEBS Letters*, 1999, pp. 341-345, vol. 452, Federation of European Biochemical Societies.

(Continued)

*Primary Examiner*—David H Kruse
(74) *Attorney, Agent, or Firm*—Womble Carlyle Sandridge & Rice, PLLC

(57) ABSTRACT

The present invention is directed to plants having increased resistance to an imidazolinone herbicide. More partitularly, the present invention includes wheat plants and triticale plants containing at least one IMI nucleic acid such as an imidazolinone resistant Brookton BR-8 or Krichauff K-42 cultivar. The present invention also includes seeds produced by these wheat plants and triticale plants and methods of controlling weeds in the vicinity of these wheat plants.

5 Claims, 7 Drawing Sheets

OTHER PUBLICATIONS

Mourad, G., et al., "Isolation and Genetic Analysis of a Triazolopyrimidine-Resistant Mutant of *Arabidopsis*," *J. Heredity*, 1993, pp. 91-96, vol. 84.

Newhouse, K., et al., "Mutations in corn (*Zea mays* L.) Conferring Resistance to Imidazolinone Herbicides," *Theor. Appl. Genet.*, 1991, pp. 65-70, vol. 83, Springer-Verlag.

Odell, et al., "Comparison of Increased Expression of Wild-Type and Herbicide-Resistant Acetolactate Synthase Genes in Transgenic Plants, and Indication of Posttranscriptional Limitation on Enzyme Activity," *Plant Physiol.*, (1990), pp. 1647-1654, vol. 94.

Ott, K., et al., "Rational Molecular Design and Genetic Engineering of Herbicide Resistant Crops by Structure Modeling and Site-directed Mutagenesis of Acetohydroxyacid Synthase," *J. Mol. Biol.*, 1996, pp. 359-368, vol. 263, Academic Press Limited.

Repellin, A., et al., "Genetic Enrichment of Cereal Crops via Alien Gene Transfer: New Challenges," *Plant Cell, Tissue and Organ Culture*, 2001, pp. 159-183, vol. 64.

Sathasivan, K., et al., "Nucleotide Sequence of a Mutant Acetolactate synthase Gene from an Imidaziolinone-resistant *Arabidopsis thaliana* var. Columbia," *Nucleic Acids Research*, 1990, pp. 2188, vol. 18(8), Oxford University Press.

Sathasivan, K., et al., "Molecular Basis of Imidazolinone Herbicide Resistance in *Arabidopsis thaliana* var Columbia," *Plant Physiol.*, 1991, pp. 1044-1050, vol. 97.

Paul R. Schmitzer et al., "Lack of Cross-Resistance of Imazaquin-Resistant *Xanthium strumarium* Acetolactate Synthase to Flumetsulam and Chlorimuron", *Plant Physiol.*, vol. 103, 1993, pp. 281-283.

Sebastian, S., et al., "Semidominant Soybean Mutation for Resistance to Sulfonylurea Herbicides," *Crop. Sci.*, 1989, pp. 1403-1408, vol. 29.

Shaner, D. and P.A. Robson, "Absorption, Translocation, and Metabolism of AC 252 214 in Soybean (*Glycine max* ), Common Cocklebur (*Xanthium strumarium* ), and Velvetleaf (*Abutilon theophrasti* )," *Weed Sci.*, 1985, pp. 469-471, vol. 33.

Shaner, D., et al., "Imidazolinones: Potent Inhibitors of Acetohydroxyacid Synthase," *Plant Physiol.*, 1984, pp. 545-546, vol. 76.

Singh, B.K., "Biosynthesis of Valine, Leucine and Isoleucine," *Plant Amino Acids*, 1999, pp. 227-247, Marcel Dekker Inc., New York, NY.

Swanson, E., et al., "Microspore Mutagenesis and Selection: Canola Plants with Field Tolerance to the Imidazolinones," *Theor. Appl. Genet.*, 1989, pp. 525-530, vol. 78, Springer-Verlag.

White, A., et al., "Common sunflower resistance to acetolactate synthase-inhibiting herbicides," *Weed Science*, 2002, pp. 432-437, vol. 50.

Wright, T.R. and D. Penner, "Cell Selection and Inheritance of Imidazolinone Resistance in Sugarbeet (*Beta vulgaris* )," *Theor. Appl. Genet.*, 1998, pp. 612-620, vol. 96, Springer-verlag.

EMBL Accession No. AF059600, Created Apr. 27, 1998.

* cited by examiner

Figure 1A

Partial nucleotide sequence of Brookton IMI1 (SEQ ID NO:1)

```
(1)    CGGCTCAGTATTACACTTACAAGCGGCCACGGCAGTGGCTGTCTTCGTCT
(51)   GGTTTGGGGGCAATGGGATTTGGGTTACCAGCTGCAGCTGGCGCTGCTGT
(101)  GGCCAACCCAGGTGTTACAGTTGTTGACATTGATGGTGATGGTAGTTTCC
(151)  TCATGAACATTCAGGAGTTGGCGTTGATCCGCATTGAGAACCTCCCAGTG
(201)  AAGGTGATGATATTGAACAACCAGCATCTGGGAATGGTGGTGCAGTGGGA
(251)  GGATAGGTTTTACAAGGCCAATCGGGCGCACACATACCTTGGCAACCCAG
(301)  AAAATGAGAGTGAGATATATCCAGATTTTGTGACGATTGCTAAAGGATTC
(351)  AACGTTCCAGCAGTTCGAGTGACGAAGAAGAGCGAAGTCACTGCAGCAAT
(401)  CAAGAAGATGCTTGAGACCCCAGGGCCATACTTGTTGGATATCATAGTCC
(451)  CGCATCAGGAGCACGTGCTGCCTATGATCCCAAACGGTGGTGCTTTCAAG
(501)  GACATGATC
```

Figure 1B

Partial deduced amino acid sequence of Brookton IMI1 (SEQ ID NO:2)

```
(1)    AQYYTYKRPRQWLSSSGLGAMGFGLPAAAGAAVANPGVTVVDIDGDGSFL
(51)   MNIQELALIRIENLPVKVMILNNQHLGMVVQWEDRFYKANRAHTYLGNPE
(101)  NESEIYPDFVTIAKGFNVPAVRVTKKSEVTAAIKKMLETPGPYLLDIIVP
(151)  HQEHVLPMIPNGGAFKDMI
```

Figure 2A

Partial nucleotide sequence of Krichauff IMI3 (SEQ ID NO:3)

```
(1)    GCGGCTCAGTATTACACTTACAAGCGGCCACGGCAGTGGCTGTCTTCGTC
(51)   TGGTTTGGGGGCAATGGGATTTGGGTTACCAGCTGCAGCTGGCGCTGCTG
(101)  TGGCCAACCCAGGTGTTACAGTTGTTGACATTGATGGAGATGGTAGTTTC
(151)  CTCATGAACATTCAGGAGTTGGCATTGATCCGTATTGAGAACCTCCCTGT
(201)  GAAGGTGATGATATTGAACAACCAGCATCTGGGAATGGTGGTGCAATGGG
(251)  AGGATAGGTTTTACAAGGCCAATCGGGCGCACACATACCTTGGCAACCCA
(301)  GAAAATGAGAGTGAGATATATCCAGATTTTGTGACGATTGCTAAAGGATT
(351)  CAACGTTCCGGCAGTTCGTGTGACGAAGAAGAGCGAAGTCACTGCAGCAA
(401)  TCAAGAAGATGCTTGAGACCCCAGGGCCATACTTGTTGGATATCATCGTC
(451)  CCGCATCAGGAGCACGTGCTGCCTATGATCCCAAACGGTGGTGCTTTCAA
(501)  GGACATGATCATGGAGGGTGATGGCAGGACCTCGTACTGAAATTTCGACC
(551)  TACAAGACCTACAAGTGTGACATGC
```

Figure 2B

Partial deduced amino acid sequence of Krichauff IMI3 (SEQ ID NO:4)

```
(1)    AAQYYTYKRPRQWLSSSGLGAMGFGLPAAAGAAVANPGVTVVDIDGDGSF
(51)   LMNIQELALIRIENLPVKVMILNNQHLGMVVQWEDRFYKANRAHTYLGNP
(101)  ENESEIYPDFVTIAKGFNVPAVRVTKKSEVTAAIKKMLETPGPYLLDIIV
(151)  PHQEHVLPMIPNGGAFKDMI
```

Figure 4

Decreased Injury of K-42 and BR-8 by Imazamox as Compared to Wild Type Varieties

|  | Wheat Cultivar | g/ha Imazamox | | |
|---|---|---|---|---|
|  |  | 0 | 40 | 120 |
| 14 DAT | Krichauff | 0.0 | 8.6 | 9.0 |
|  | K-42 | 0.0 | 5.1 | 7.8 |
|  | Brookton | 0.0 | 9.0 | 9.0 |
|  | BR-8 | 0.0 | 5.6 | 7.0 |
| 21 DAT | Krichauff | 0.0 | 9.0 | 9.0 |
|  | K-42 | 0.0 | 4.1 | 7.6 |
|  | Brookton | 0.0 | 9.0 | 9.0 |
|  | BR-8 | 0.0 | 4.5 | 6.5 |

Figure 5

Inhibition of AHAS Enzyme Activity in Wild Type Wheat
(variety Brookton or Krichauff) and BR-8 and K-42

| Imazamox (µM) | % Uninhibited AHAS Activity | | | |
|---|---|---|---|---|
| | Brookton | Br-8 | Krichauff | K-42 |
| 1.6 | 73.2 | 79.7 | 84.3 | 78.7 |
| 3.1 | 62.9 | 73.7 | 74.6 | 76.0 |
| 6.3 | 47.6 | 61.2 | 53.3 | 67.0 |
| 12.5 | 30.2 | 56.0 | 30.5 | 53.8 |
| 25.0 | 24.4 | 50.0 | 25.3 | 50.4 |
| 50.0 | 15.2 | 48.4 | 17.6 | 49.0 |
| 100.0 | 14.7 | 48.1 | 16.9 | 47.4 |

Figure 6

Decreased Injury of K-42/BR-8 Hybrid by Imazamox as Compared to Wild Type Varieties
and Parental Lines K-42 and BR-8

| | Injury rating 14 and 21 DAT at three imazamox rates (g/ha) | | | | | |
|---|---|---|---|---|---|---|
| | 14 DAT | | | 21 DAT | | |
| Line | 0 | 40 | 120 | 0 | 40 | 120 |
| Krichauff | 0.0 | 8.6 | 9.0 | 0.0 | 9.0 | 9.0 |
| Brookton | 0.0 | 9.0 | 9.0 | 0.0 | 9.0 | 9.0 |
| K-42 | 0.0 | 5.1 | 7.8 | 0.0 | 4.1 | 7.6 |
| Br-8 | 0.0 | 5.6 | 7.0 | 0.0 | 4.5 | 6.5 |
| K-42/Br-8 | 0.0 | 0.2 | 1.4 | 0.0 | 0.0 | 0.3 |

Figure 7

Inhibition of AHAS Enzyme Activity in Wild Type Wheat
(variety Brookton or Krichauff) and BR-8/K-42 Hybrid and Parental Lines K-42 and BR-8

|  | % Uninhibited AHAS Activity | | | | |
|---|---|---|---|---|---|
| μM Imazethapyr | Brookton | Krichauff | Br-8 | K-42 | Br-8/K-42 |
| 1.6 | 71.1 | 84.3 | 61.7 | 79.7 | 80.1 |
| 3.1 | 60.7 | 74.6 | 53.0 | 73.7 | 68.8 |
| 6.3 | 43.5 | 53.3 | 47.1 | 61.2 | 61.9 |
| 12.5 | 27.3 | 30.5 | 40.9 | 48.4 | 57.9 |
| 25.0 | 22.8 | 25.3 | 39.7 | 44.4 | 60.0 |
| 50.0 | 17.7 | 17.6 | 36.9 | 37.7 | 58.7 |
| 100.0 | 16.8 | 16.9 | 35.9 | 36.6 | 60.3 |

WHEAT PLANTS HAVING INCREASED RESISTANCE TO IMIDAZOLINONE HERBICIDES

CROSS-REFERENCE TO RELATED APPLICATIONS

This application is the U.S. National Stage of International Application No. PCT/IB2003/004645, filed Jul. 9, 2003; which claims the benefit of U.S. Provisional Application No. 60/394,991, filed Jul. 10, 2002.

FIELD OF THE INVENTION

The present invention relates in general to plants having an increased resistance to imidazolinone herbicides. More specifically, the present invention relates to wheat plants obtained by mutagenesis and cross-breeding and transformation that have an increased resistance to imidazolinone herbicides.

BACKGROUND OF THE INVENTION

Acetohydroxyacid synthase (AHAS; EC 4.1.3.18, acetolactate synthase (ALS)), encoded by the Als nucleic acid, is the first enzyme that catalyzes the biochemical synthesis of the branched chain amino acids valine, leucine, and isoleucine (Singh B. K., 1999, Biosynthesis of valine, leucine and isoleucine in: Singh B. K. (Ed) Plant amino acids. Marcel Dekker Inc. New York, N.Y. Pg 227-247). AHAS is the site of action of four structurally diverse herbicide families including the sulfonylureas (LaRossa R A and Falco S C, 1984, Trends Biotechnol. 2:158-161), the imidazolinones (Shaner et al., 1984, Plant Physiol. 76:545-546), the triazolopyrimidines (Subramanian and Gerwick, 1989, Inhibition of acetolactate synthase by triazolopyrimidines in (ed) Whitaker J R, Sonnet P E Biocatalysis in agricultural biotechnology. ACS Symposium Series, American Chemical Society. Washington, D.C. Pg 277-288), and the pyrimidyloxybenzoates (Subramanian et al., 1990, Plant Physiol. 94: 239-244.). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tubenuron methyl, bensulfuron methyl, nicosufuron, ethametsulfuron methyl, rimsulfuron, triflusulfuron methyl, triasulfuron, primisulfuron methyl, cinosulfuron, amidosulfuron, fluzasulfuron, imazosulfuron, pyrazosulfuron ethyl, and halosulfuron.

Due to their high effectiveness and low toxicity, imidazolinone herbicides are favored for application by spraying over the top of a wide area of vegetation. The ability to spray an herbicide over the top of a wide range of vegetation decreases the costs associated with plantation establishment and maintenance, and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robson, 1985, Weed Sci. 33:469-471). Other crops such as corn (Newhouse et al., 1992, Plant Physiol. 100:882-886) and rice (Barrett et al., 1989, Crop Safeners for Herbicides, Academic Press New York, pp. 195-220) are susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al., 1984, Plant Physiol. 76:545-546; Brown et al., 1987, Pestic. Biochem. Physiol. 27:24-29). Other plant physiological differences such as absorption and translocation also play an important role in sensitivity (Shaner and Robson, 1985, Weed Sci. 33:469-471).

Crop cultivars resistant to imidazolinones, sulfonylureas and triazolopyrimidines have been successfully produced using seed, microspore, pollen, and callus mutagenesis in *Zea mays*, *Brassica napus*, *Glycine max*, and *Nicotiana tabacum* (Sebastian et al., 1989, Crop Sci. 29:1403-1408; Swanson et al., 1989, Theor. Appl. Genet 78:525-530; Newhouse et al., 1991, Theor. Appl. Genet 83:65-70; Sathasivan et al., 1991, Plant Physiol. 97:1044-1050; Mourad et al., 1993, J. Heredity 84:91-96). In all cases, a single, partially dominant nuclear gene conferred resistance. Four imidazolinone resistant wheat plants were also previously isolated following seed mutagenesis of *Triticum aestivum* L. cv Fidel (Newhouse et al., 1992, Plant Physiol. 100:882-886). Inheritance studies confirmed that a single, partially dominant gene conferred resistance. Based on allelic studies, the authors concluded that the mutations in the four identified lines were located at the same locus. One of the Fidel cultivar resistance genes was designated FS-4 (Newhouse et al., 1992, Plant Physiol. 100: 882-886).

Computer-based modeling of the three dimensional conformation of the AHAS-inhibitor complex predicts several amino acids in the proposed inhibitor binding pocket as sites where induced mutations would likely confer selective resistance to imidazolinones (Ott et al., 1996, J. Mol. Biol. 263: 359-368). Tobacco plants produced with some of these rationally designed mutations in the proposed binding sites of the AHAS enzyme have in fact exhibited specific resistance to a single class of herbicides (Ott et al., 1996, J. Mol. Biol. 263:359-368).

Plant resistance to imidazolinone herbicides has also been reported in a number of patents. U.S. Pat. Nos. 4,761,373, 5,331,107, 5,304,732, 6,211,438, 6,211,439, and 6,222,100 generally describe the use of an altered Als nucleic acid to elicit herbicide resistance in plants, and specifically disclose certain imidazolinone resistant corn lines. U.S. Pat. No. 5,013,659 discloses plants exhibiting herbicide resistance possessing mutations in at least one amino acid in one or more conserved regions. The mutations described therein encode either cross-resistance for imidazolinones and sulfonylureas or sulfonylurea-specific resistance, but imidazolinone-specific resistance is not described. Additionally, U.S. Pat. No. 5,731,180 and U.S. Pat. No. 5,767,361 discuss an isolated gene having a single amino acid substitution in a wild-type monocot AHAS amino acid sequence that results in imidazolinone-specific resistance.

To date, the prior art has not described imidazolinone resistant wheat or triticale plants comprising at least one altered Als nucleic acid from a *Triticum aestivum* Brookton or Krichauff cultivar. Nor has the prior art described imidazolinone resistant wheat plants containing mutations on genomes other than the genome from which the FS-4 gene is derived. Therefore, what is needed in the art is the identification of imidazolinone resistance genes from additional genomes. What are also needed in the art are wheat plants and triticale plants having increased resistance to herbicides such as imidazolinone and containing at least one altered Als nucleic acid. Also needed are methods for controlling weed growth in the vicinity of such wheat plants and triticale plants. These compositions and methods would allow for the use of spray over techniques when applying herbicides to areas containing wheat plants and triticale plants.

SUMMARY OF THE INVENTION

The present invention provides wheat plants comprising IMI nucleic acids, wherein the wheat plant has increased resistance to an imidazolinone herbicide as compared to a wild-type variety of the plant. The wheat plants can contain one, two, three, or more IMI alleles. In one embodiment, the wheat plant comprises at least one IMI nucleic acid. In another embodiment, the at least one IMI nucleic acid is selected from the group consisting of an Imi1 nucleic acid, an Imi2 nucleic acid, and an Imi3 nucleic acid. In another embodiment, the at least one IMI nucleic acid comprises a *Triticum aestivum* IMI nucleic acid. In another embodiment, the at least one IMI nucleic acid comprises a Brookton or Krichauff cultivar IMI nucleic acid. In yet another embodiment, the wheat plant comprises multiple IMI nucleic acids located on different genomes. In another embodiment, the multiple IMI nucleic acids comprise a *Triticum aestivum* Imi1 nucleic acid and a *Triticum aestivum* Imi3 nucleic acid. In another embodiment, the multiple IMI nucleic acids comprise a Brookton cultivar Imi1 nucleic acid and a Krichauff cultivar Imi3 nucleic acid. Preferably, the IMI nucleic acids encode proteins comprising a mutation in a conserved amino acid sequence selected from the group consisting of a Domain A, a Domain B, a Domain C, a Domain D, and a Domain E. More preferably, the mutation is in a conserved Domain. Also provided are plant parts and plant seeds derived from the wheat plants described herein.

The present invention also provides triticale plants comprising IMI nucleic acids, wherein the triticale plant has increased tolerance to an imidazolinone herbicide as compared to a wild-type variety of the triticale plant. In one embodiment, the triticale plant comprises at least one IMI nucleic acid. In another embodiment, the at least one IMI nucleic acid is selected from the group consisting of an Imi1 nucleic acid, an Imi2 nucleic acid, and an Imi3 nucleic acid. In another embodiment, the at least one IMI nucleic acid comprises a *Triticum aestivum* Brookton or Krichauff cultivar IMI nucleic acid. In another embodiment, the wheat plant comprises multiple IMI nucleic acids located on different genomes. In yet another embodiment, the multiple IMI nucleic acids comprise a Brookton cultivar Imi1 nucleic acid and a Krichauff cultivar Imi3 nucleic acid. In another embodiment, the IMI nucleic acids encode proteins comprising a mutation in a conserved amino acid sequence selected from the group consisting of a Domain A, a Domain B, a Domain C, a Domain D, and a Domain E. More preferably, the mutation is in a conserved Domain E. Also provided are plant parts and plant seeds derived from the triticale plants described herein.

The IMI nucleic acids of the present invention can comprise a polynucleotide sequence selected from the group consisting of: a polynucleotide as defined in SEQ ID NO:1; a polynucleotide as defined in SEQ ID NO:3; a polynucleotide sequence encoding a polypeptide as defined in SEQ ID NO:2; a polynucleotide sequence encoding a polypeptide as defined in SEQ ID NO:4; a polynucleotide comprising at least 60 consecutive nucleotides of any of the aforementioned polynucleotides; and a polynucleotide complementary to any of the aforementioned polynucleotides.

The plants of the present invention can be transgenic or non-transgenic. Examples of non-transgenic wheat plants having increased resistance to imidazolinone herbicides include a wheat plant having an ATCC Patent Deposit Designation Number PTA-4256 or PTA-4257; or a mutant, recombinant, or genetically engineered derivative of the plant with ATCC Patent Deposit Designation Number PTA-4256 or PTA-4257; or of any progeny of the plant with ATCC Patent Deposit Designation Number PTA-4256 or PTA-4257; or a plant that is a progeny of any of these plants.

In addition to the compositions of the present invention, several methods are provided. Described herein are methods of modifying a plant's tolerance to an imidazolinone herbicide comprising modifying the expression of an IMI nucleic acid in the plant. Also described are methods of producing a transgenic plant having increased tolerance to an imidazolinone herbicide comprising, transforming a plant cell with an expression vector comprising one or more IMI nucleic acids and generating the plant from the plant cell. The invention further includes a method of controlling weeds within the vicinity of a wheat plant, comprising applying an imidazolinone herbicide to the weeds and to the wheat plant, wherein the wheat plant has increased resistance to the imidazolinone herbicide as compared to a wild type variety of the wheat plant and wherein the plant comprises one or more IMI nucleic acids. In some preferred embodiments of these methods, the plants comprise multiple IMI nucleic acids that are located on different wheat genomes.

BRIEF DESCRIPTION OF THE DRAWINGS

FIGS. 1A-B show the partial cDNA sequence of the Brookton BR-8 Imi1 nucleic acid (SEQ ID NO:1) and the deduced amino acid sequence thereof (SEQ ID NO:2).

FIGS. 2A-B show the partial cDNA sequence of Krichauff K-42 Imi3 nucleic acid (SEQ ID NO:3) and the deduced amino acid sequence thereof (SEQ ID NO:4).

FIG. 4 is a table showing the increased resistance and decreased injury of K-42 and BR-8 wheat cultivars to the imidazolinone herbicide imazamox relative to their respective wild type counterparts.

FIG. 5 is a table showing the inhibition of AHAS enzyme activity in wild-type wheat (variety Brookton or Krichauff), Br-8 and K-42 by imidazolinone herbicide imazamox. Values are expressed as a percent of uninhibited activity.

FIG. 6 is a table showing increased resistance and decreased injury of a K-42/BR-8 hybrid wheat cultivar to the imidazolinone herbicide imazamox, relative to the parental lines K-42 and BR-8.

FIG. 7 is a table showing the inhibition of AHAS enzyme activity in wild-type wheat (variety Brookton or Krichauff), Br-8, K-42 and Br-8/K-42 by imidazolinone herbicide imazamox. Values are expressed as a percent of uninhibited activity.

DETAILED DESCRIPTION

Figure 3:
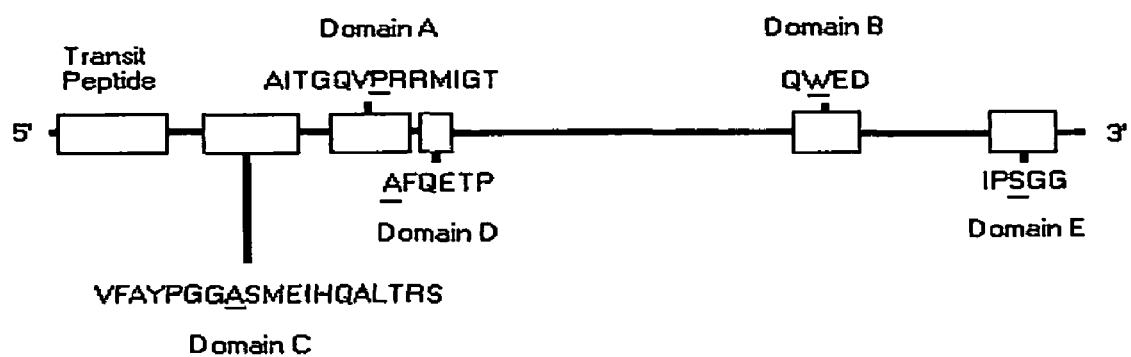
FIG. 3 is a schematic representation of the conserved amino acid sequences in the AHAS genes implicated in resistance to various AHAS inhibitors. The specific amino acid site responsible for resistance is indicated by an underline. (Modified from Devine, M. D. and Eberlein, C. V., 1997, Physiological, biochemical, and molecular aspects of herbicide resistance based on altered target sites in Herbicide Activity: Toxicity, Biochemistry, and Molecular Biology, IOS Press Amersterdam, p. 159-185).

The present invention is directed to wheat plants, wheat plant parts and wheat plant cells having increased resistance to imidazolinone herbicides. The present invention also includes seeds produced by the wheat plants described herein and methods for controlling weeds in the vicinity of the wheat plants described herein. It is to be understood that as used in the specification and in the claims, "a" or "an" can mean one or more, depending upon the context in which it is used. Thus, for example, reference to "a cell" can mean that at least one cell can be utilized.

As used herein, the term "wheat plant" refers to a plant that is a member of the *Triticum* genus. The wheat plants of the present invention can be members of a *Triticum* genus including, but not limited to, *T. aestivum, T. turgidum, T. timopheevii, T. monococcum, T. zhukovskyi* and *T. urartu* and hybrids thereof. Examples of *T. aestivum* subspecies included within the present invention are *aestivum* (common wheat), *compactum* (club wheat), *macha* (macha wheat), *vavilovi* (vavilovi wheat), *spelta* and *sphaerococcum* (shot wheat). Examples of *T. turgidum* subspecies included within the present invention are *turgidum, carthlicum, dicocconm, durum, paleocolchicum, polonicum, turanicum*, and *dicoccoides*. Examples of *T. monococcum* subspecies included within the present invention are *monococcum* (einkorn) and *aegilopoides*. In one embodiment of the present invention, the wheat plant is a member of the *Triticum aestivum* L. species, and more particularly, a Brookton or Krichauff cultivar.

The term "wheat plant" is intended to encompass wheat plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like. The present invention also includes seeds produced by the wheat plants of the present invention. In one embodiment, the seeds are true breeding for an increased resistance to an imidazolinone herbicide as compared to a wild type variety of the wheat plant seed.

The present invention also encompasses triticale plants, triticale plant parts, and triticale plant cells having increased tolerance to imidazolinone herbicides. As used herein, a "triticale plant" refers to a plant that is created by crossing a rye plant (*Secale cereale*) with either a tetraploid wheat plant (e.g. *Triticum turgidum*) or a hexaploid wheat plant (e.g. *Triticum aestivum*). The present invention also includes seeds produced by the triticale plants described herein and methods for controlling weeds in the vicinity of the triticale plants described herein.

The present invention describes a wheat plant comprising at least one IMI nucleic acid, wherein the wheat plant has increased tolerance to an imidazolinone herbicide as compared to a wild-type variety of the plant. It is possible for the wheat plants of the present invention to have multiple IMI nucleic acids from different genomes since these plants can contain more than one genome. For example, a *Triticum aestivum* wheat plant contains three genomes sometimes referred to as the A, B, and D genomes. Because AHAS is a required metabolic enzyme, it is assumed that each genome has at least one gene coding for the AHAS enzyme (i.e. at least one Als gene), commonly seen with other metabolic enzymes in hexaploid wheat that have been mapped. As used herein, the term "Als gene locus" refers to the position of an Als gene on a genome, and the terms "Als gene" and "Als nucleic acid" refer to a nucleic acid encoding the AHAS enzyme. The Als nucleic acid on each genome differs in its nucleotide sequence from an Als nucleic acid on another genome. One of skill in the art can determine the genome of origin of each Als nucleic acid through genetic crossing and/or either sequencing methods or exonuclease digestion methods known to those of skill in the art. As used herein, the terms "Als1 nucleic acid," "Als2 nucleic acid," and "Als3 nucleic acid" refer to Als nucleic acids located on three different genomes. For the purposes of this invention, the Als3 gene locus is located on the A genome, the Als2 gene locus is located on the B genome, and the Als1 gene locus is located on the D genome. Also for the purposes of this invention, IMI nucleic acids derived from the A, B, or D genomes are distinguished and designated as Imi1, Imi2, or Imi3 nucleic acids, respectively.

As used herein, the term "IMI nucleic acid" refers to an Als nucleic acid having a sequence that is mutated from a wild type Als nucleic acid and that confers increased imidazolinone tolerance to a plant in which it is expressed. As used herein, the terms "Imi1 nucleic acid," "Imi2 nucleic acid," and "Imi3 nucleic acid" are IMI nucleic acids that refer to the imidazolinone tolerance alleles of the Als1, Als2, and Als3 genes, respectively. Because wheat plants have two copies of each genome, a wheat plant contains two copies of each particular Als nucleic acid. For example, a *Triticum aestivum* wheat plant comprises two copies each of the A, B, and D genomes, and therefore, two copies each of the Als3, Als2, and Als1 genes. As used herein, the term "IMI allele" refers to a single copy of a particular IMI nucleic acid. Accordingly, for the purposes of the present invention, a wheat plant may have two Imi2 alleles, one on each of two copies of the B genome.

In another embodiment, the wheat plant comprises multiple IMI nucleic acids. As used herein, when describing a plant that comprises "multiple IMI nucleic acids," the phrase "multiple IMI nucleic acids" refers to the presence of different IMI nucleic acids in the plant and not to whether the plant is homozygous or heterozygous at a particular Als locus. For example, a plant comprising multiple IMI nucleic acids may comprise an Imi2 and an Imi3 nucleic acid, as opposed to having two copies of an Imi2 nucleic acid.

The Imi1 class of nucleic acids includes the FS-4 gene as described by Newhouse et al. (1992 Plant Physiol. 100:882-886) and the Brookton IMI1 BR-8 gene described in more detail below. The Imi3 class of nucleic acids includes the Krichauff IMI3 K-42 gene described below. Each Imi class can include members from different wheat species. Therefore, each Imi class includes IMI nucleic acids that differ in their nucleotide sequence but that are nevertheless designated as originating from, or being located on, the same wheat genome using inheritance studies as known to those of ordinary skill in the art.

Accordingly, the present invention includes a wheat plant comprising at least one IMI nucleic acid, wherein the wheat plant has increased resistance to an imidazolinone herbicide as compared to a wild-type variety of the plant and wherein the at least one IMI nucleic acid is selected from the group consisting of an Imi1 nucleic acid, an Imi2 nucleic acid, and imi3 nucleic acid. In one embodiment, the plant comprises an Imi1 nucleic and an Imi3 nucleic acid. In a preferred embodiment, the Imi1 nucleic acid comprises the polynucleotide sequence shown in SEQ ID NO:1, and the Imi3 nucleic acid comprises the polynucleotide sequence shown in SEQ ID NO:3. In another embodiment, the plant comprises an Imi2 nucleic acid.

The present invention also encompasses an imidazolinone tolerant triticale plant. As used herein, a "triticale plant" refers to a plant that is created by crossing a rye plant (*Secale cereale*) with either a tetraploid wheat plant (e.g. *Triticum turgidum*) or a hexaploid wheat plant (e.g. *Triticum aestivum*). For the purposes of the present invention, an imidazolinone tolerant triticale plant comprises at least one IMI nucleic acid, wherein the triticale plant has increased tolerance to an imidazolinone herbicide as compared to a wild-type variety of the plant and wherein the at least one IMI nucleic acid is selected from a group consisting of an Imi1 nucleic acid, an Imi2 nucleic acid, and an Imi3 nucleic acid. In one embodiment, the plant comprises both an Imi1 nucleic acid and an Imi3 nucleic acid. In a preferred embodiment, the Imi1 nucleic acid comprises the polynucleotide sequence of SEQ ID NO:1. In another preferred embodiment, the Imi3 nucleic acid comprises the polynucleotide sequence of SEQ ID NO:3.

As used herein with regard to nucleic acids, the term "from" refers to a nucleic acid "located on" or "derived from" a particular genome. The term "located on" refers to a nucleic acid contained within that particular genome. As also used herein with regard to a genome, the term "derived from" refers to a nucleic acid that has been removed or isolated from that genome. The term "isolated" is defined in more detail below.

The present invention includes wheat plants comprising one, two, three, or more IMI alleles, wherein the wheat plant has increased resistance to an imidazolinone herbicide as compared to a wild-type variety of the plant. The IMI alleles can comprise a nucleotide sequence selected from the group consisting of a polynucleotide as defined in SEQ ID NO:1; a polynucleotide as defined in SEQ ID NO:3; a polynucleotide encoding a polypeptide as defined in SEQ ID NO:2; a polynucleotide encoding a polypeptide as defined in SEQ ID NO:4; a polynucleotide comprising at least 60 consecutive nucleotides of any of the aforementioned polynucleotides; and a polynucleotide complementary to any of the aforementioned polynucleotides.

The present invention also includes triticale plants comprising one, two, three, or more IMI alleles, wherein the triticale plant has increased tolerance to an imidazolinone herbicide as compared to a wild-type variety of the plant. The MI alleles can comprise a polynucleotide sequence selected from the group consisting of a polynucleotide as defined in SEQ ID NO:1 or SEQ ID NO:3; a polynucleotide encoding a polypeptide as defined in SEQ ID NO:2 or SEQ ID NO:4; a polynucleotide comprising at least 60 consecutive nucleotides of any of the aforementioned polynucleotides; and a polynucleotide complementary to any of the aforementioned polynucleotides.

In one embodiment, the wheat plant or triticale plant comprises two different IMI nucleic acids, wherein the nucleic acids are derived from or located on different wheat genomes. Preferably, the two nucleic acids are an Imi1 nucleic acid and an Imi3 nucleic acid. More preferably, the Imi1 nucleic acid comprises the polynucleotide sequence of SEQ ID NO:1, and the Imi3 nucleic acid comprises the polynucleotide sequence of SEQ ID NO:3. In another embodiment, the wheat plant or triticale plant comprises one IMI nucleic acid, wherein the nucleic acid comprises the polynucleotide sequence of SEQ ID NO:1 or SEQ ID NO:3. In yet another embodiment, the wheat plant comprises greater than two IMI nucleic acids wherein each IMI nucleic acid is from a different genome. Preferably, at least one of the IMI nucleic acids comprises a polynucleotide sequence selected from the group consisting of SEQ ID NO:1 and SEQ ID NO:3.

In a preferred embodiment of the present invention, the isolated IMI nucleic acid encodes an amino acid sequence comprising a mutation in a domain that is conserved among several AHAS proteins. These conserved domains are referred to herein as Domain A, Domain B, Domain C, Domain D, and Domain E. FIG. 3 shows the general location of each domain in an AHAS protein. Domain A contains the amino acid sequence AITGQVPRRMIGT (SEQ ID NO:5). Domain B contains the amino acid sequence QWED (SEQ ID NO:6). Domain C contains the amino acid sequence VFAYPGGASMEIHQALTRS (SEQ ID NO:7). Domain D contains the amino acid sequence AFQETP (SEQ ID NO:8). Domain E contains the amino acid sequence IPSGG (SEQ ID NO:9). The present invention also contemplates that there may be slight variations in the conserved domains, for example, in cockleber plants, the serine residue in Domain E is replaced by an alanine residue.

Accordingly, the present invention includes a wheat plant or triticale plant comprising an IMI nucleic acid that encodes an amino acid sequence having a mutation in a conserved domain selected from the group consisting of a Domain A, a Domain B, a Domain C, a Domain D, and a Domain E. In one embodiment, the wheat plant or triticale plant comprises an IMI nucleic acid that encodes an amino acid sequence having a mutation in a Domain E. In further preferred embodiments, the mutations in the conserved domains occur at the locations indicated by the following underlining: AITGQV<u>P</u>RRMIGT (SEQ ID NO:5); Q<u>W</u>ED (SEQ ID NO:6); VFAYPGG<u>A</u>SMEIHQALTRS (SEQ ID NO:7); <u>A</u>FQETP (SEQ ID NO:8), and IP<u>S</u>GG (SEQ ID NO:9). One preferred substitution is asparagine for serine in Domain E.

The imidazolinone herbicide can be selected from, but is not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, or a mixture of two or more of the aforementioned herbicides, for example, imazapyr/imazamox (ODYSSEY®). More specifically, the imidazolinone herbicide can be selected from, but is not limited to, 2-(4-isopropyl-4-methyl-5-oxo-2-imidiazolin-2-yl)-nicotinic acid, 2-(4-isopropyl)-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate and methyl 2-(4-isopropyl4-methyl-5-oxo-2-imidazolin-2-yl)-p-toluate. The use of 5-ethyl-2-(4-isopropyl4-methyl-5-oxo-2-imidazolin-2-yl)-nicotinic acid and 2-(4-isopropyl4-methyl-5-oxo-2-imidazolin-2-yl)-5-(methoxymethyl)-nicotinic acid is preferred. The use of 2-(4-isopropyl4-methyl-5-oxo-2-imidazolin-2-yl)-5-(methoxymethyl)-nicotinic acid is particularly preferred.

The wheat plants described herein can be either transgenic wheat plants or non-transgenic wheat plants. Similarly, the triticale plants described herein can be either transgenic triticale plants or non-transgenic triticale plants. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding. Plants containing mutations arising due to non-spontaneous mutagenesis and selective breeding are referred to herein as non-transgenic plants and are included in the present invention. In embodiments wherein the wheat plant is transgenic and comprises multiple IMI nucleic acids, the nucleic acids can be derived from different genomes or from the same genome. Alternatively, in embodiments wherein the wheat plant is non-transgenic and comprises multiple IMI nucleic acids, the nucleic acids are located on different genomes or on the same genome.

An example of a non-transgenic wheat plant cultivar comprising one IMI nucleic acid is the plant cultivar deposited with the ATCC under Patent Deposit Designation Number PTA-4256 and designated herein as the Brookton IMI BR-8 wheat cultivar. The Brookton IMI BR-8 wheat cultivar contains an Imi1 nucleic acid. The partial nucleotide sequence corresponding to the Brookton IMI BR-8 gene is shown in SEQ ID NO:1.

Another example of a non-transgenic wheat plant cultivar comprising one IMI nucleic acid is the plant cultivar deposited with the ATCC under Patent Deposit Designation Number PTA4257 and designated herein as the Krichauff IMI K-42 wheat cultivar. The Krichauff IMI K-42 wheat cultivar contains an Imi3 nucleic acid. The partial nucleotide sequence corresponding to the Krichauff IMI K-42 gene is shown in SEQ ID NO:3.

Separate deposits of 2500 seeds of the Brookton IMI BR-8 and Krichauff IMI K-42 wheat cultivars were made with the American Type Culture Collection, Manassas, Va. on May 1, 2002. These deposits were made in accordance with the terms and provisions of the Budapest Treaty relating to the deposit of microorganisms. The deposits were made for a term of at least thirty years and at least five years after the most recent request for the furnishing of a sample of the deposit is received by the ATCC. The deposited seeds were accorded Patent Deposit Designation Numbers PTA4256 (Brookton IMI BR-8 ) and PTA4257 (Krichauff IMI K-42).

The present invention includes the wheat plant having a Patent Deposit Designation Number PTA4256 or PTA4257; a mutant, recombinant, or genetically engineered derivative of the plant with Patent Deposit Designation Number PTA-4256 or PTA-4257; any progeny of the plant with Patent Deposit Designation Number PTA-4256 or PTA-4257; and a plant that is the progeny of any of these plants. In a preferred embodiment, the wheat plant of the present invention additionally has the herbicide resistance characteristics of the plant with Patent Deposit Designation Number PTA-4256 or PTA-4257.

Also included in the present invention are hybrids of the Brookton IMI BR-8 and Krichauff IMI K-42 wheat plants described herein and hybrids of the Brookton IMI BR-8 or Krichauff IMI K-42 with another wheat plant. The other wheat plant includes, but is not limited to, *T. aestivum* L. cv Fidel and any wheat plant harboring a mutant gene FS-1, FS-2, FS-3 or FS4. (See U.S. Pat. No. 6,339,184 and U.S. patent application Ser. No. 08/474,832). Preferred Brookton IMI BR-8/Krichauff IMI K-42 hybrids comprise an Imi1 nucleic acid and an Imi3 nucleic acid.

The terms "cultivar" and "variety" refer to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in an Als gene of the wheat or triticale plant or seed.

It is to be understood that the wheat or triticale plant of the present invention can comprise a wild type Als nucleic acid in addition to an IMI nucleic acid. As described in Example 1, it is contemplated that the Brookton IMI BR-8 and Krichauff IMI K-42 wheat cultivars contain a mutation in only one of multiple AHAS isoenzymes. Therefore, the present invention includes a wheat plant or triticale plant comprising at least one IMI nucleic acid in addition to one or more wild type Als nucleic acids.

In addition to wheat and triticale plants, the present invention encompasses isolated IMI proteins and nucleic acids. The nucleic acids comprise a polynucleotide selected from the group consisting of a polynucleotide as defined in SEQ ID NO:1; a polynucleotide as defined in SEQ ID NO:3; a polynucleotide encoding of a polypeptide as defined in SEQ ID NO:2; a polynucleotide encoding of a polypeptide as defined in SEQ ID NO:4; a polynucleotide comprising at least 60 consecutive nucleotides of any of the aforementioned polynucleotides; and a polynucleotide complementary to any of the aforementioned polynucleotides. In a preferred embodiment, the IMI nucleic acid comprises a polynucleotide sequence of SEQ ID NO:1 or SEQ ID NO:3.

The term "AHAS protein" or "AHAS polypeptide" refers to an acetohydroxyacid synthase protein, and the terms "IMI protein" or "IMI polypeptide" refes to any AHAS protein that is mutated from a wild type AHAS protein and that confers increased imidazolinone resistance to a plant, plant cell, plant part, plant seed, or plant tissue when it is expressed therein. In a preferred embodiment, the IMI protein comprises a polypeptide encoded by a polynucleotide sequence comprising SEQ ID NO:1. In another preferred embodiment, the IMI protein comprises a polypeptide encoded by a polynucleotide sequence comprising SEQ ID NO:3. In still another preferred embodiment, the IMI protein comprises a polypeptide comprising SEQ ID NO:2 or SEQ ID NO:4. As also used herein, the terms "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences that naturally flank the nucleic acid (i.e., sequences located at the 5' and 3' ends of the nucleic acid) in its naturally occurring replicon. For example, a cloned nucleic acid is considered isolated. In various embodiments, the isolated IMI nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Triticum aestivum* cell). A nucleic acid is also considered isolated if it has been altered by human intervention, or placed in a locus or location that is not its natural site, or if it is introduced into a cell by agroinfection, biolistics, or any other method of plant transformation. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule containing a nucleotide sequence of SEQ ID NO:1, SEQ ID NO:3 or a portion thereof, can be isolated using standard molecular biology techniques and the sequence information provided herein. For example, a *T. aestivum* IMI cDNA can be isolated from a *T. aestivum* library using all or a portion of the sequence of SEQ ID NO:1 or SEQ ID NO:3. Moreover, a nucleic acid molecule encompassing all or a portion of SEQ ID NO:1 or SEQ ID NO:3 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294-5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1 or SEQ ID NO:3. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an IMI nucleotide sequence can be prepared by standard synthetic techniques, e.g., using an automated DNA synthesizer.

The IMI nucleic acids of the present invention can comprise sequences encoding an IMI protein (i.e., "coding regions"), as well as 5' untranslated sequences and 3' untranslated sequences. Alternatively, the nucleic acid molecules of the present invention can comprise only the coding regions of an IMI gene, or can contain whole genomic fragments isolated from genomic DNA. A coding region of these sequences is indicated as an "ORF position." Moreover, the nucleic acid molecule of the invention can comprise a portion of a coding region of an IMI gene, for example, a fragment that can be used as a probe or primer. The nucleotide sequences determined from the cloning of the IMI genes from *T. aestivum* allow for the generation of probes and primers designed for use in identifyng and/or cloning IMI homologs in other cell types and organisms, as well as IMI homologs from other wheat plants and related species. The portion of the coding region can also encode a biologically active fragment of an IMI protein.

As used herein, the term "biologically active portion of" an IMI protein is intended to include a portion, e.g., a domain/motif, of an IMI protein that, when produced in a plant increases the plant's resistance to an imidazolinone herbicide as compared to a wild-type variety of the plant. Methods for quantitating increased resistance to imidazolinone herbicides are provided in the Examples below. Biologically active portions of an EVU protein include peptides derived from SEQ ID NO:2 or SEQ ID NO:4 which include fewer amino acids than a full length IMI protein and impart increased resistance to an imidazolinone herbicide upon expression in a plant. Typically, biologically active portions (e.g., peptides which are, for example, 5, 10, 15, 20, 30, 35, 36, 37, 38, 39, 40, 50, 100, or more amino acids in length) comprise a domain or motif with at least one activity of an IMI protein. Moreover, other biologically active portions in which other regions of the polypeptide are deleted, can be prepared by recombinant techniques and evaluated for one or more of the activities described herein. Preferably, the biologically active portions of an IMI protein include one or more conserved domains selected from the group consisting of a Domain A, a Domain B, a Domain C, a Domain D and a Domain E, wherein the conserved domain contains a mutation.

The invention also provides IMI chimeric or fusion polypeptides. As used herein, an IMI "chimeric polypeptide" or "fusion polypeptide" comprises an IMI polypeptide operatively linked to a non-IMI polypeptide. A "non-IMI polypeptide" refers to a polypeptide having an amino acid sequence that is not substantially identical to an IMI polypeptide, e.g., a polypeptide that is not an IMI isoenzyme, which peptide performs a different function than an IMI polypeptide. As used herein with respect to the fusion polypeptide, the term "operatively linked" is intended to indicate that the IMI polypeptide and the non-IMI polypeptide are fused to each other so that both sequences fulfill the proposed function attributed to the sequence used. The non-IMI polypeptide can be fused to the N-terminus or C-terminus of the IMI polypeptide. For example, in one embodiment, the fusion polypeptide is a GST-IMI fusion polypeptide in which the IMI sequence is fused to the C-terminus of the GST sequence. Such fusion polypeptides can facilitate the purification of recombinant IMI polypeptides. In another embodiment, the fusion polypeptide is an IMI polypeptide containing a heterologous signal sequence at its N-terminus. In certain host cells (e.g., mammalian host cells), expression and/or secretion of an IMI polypeptide can be increased through use of a heterologous signal sequence.

An isolated nucleic acid molecule encoding an IMI polypeptide having a certain percent sequence identity to a polypeptide of SEQ ID NO:2 or SEQ ID NO:4 can be created by introducing one or more nucleotide substitutions, additions, or deletions into a nucleotide sequence of SEQ ID NO:1 or SEQ ID NO:3 such that one or more amino acid substitutions, additions, or deletions are introduced into the encoded polypeptide. Mutations can be introduced into a sequence of SEQ ID NO:1 or SEQ ID NO:3 by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an IMI polypeptide is preferably replaced with another amino acid residue from the same side chain family. Alternatively, in another embodiment, mutations can be introduced randomly along all or part of an IMI coding sequence, such as by saturation mutagenesis, and the resultant mutants can be screened for an IMI activity described herein to identify mutants that retain IMI activity. Following mutagenesis of the sequence of SEQ ID NO:1 or SEQ ID NO:3, the encoded polypeptide can be expressed recombinantly and the activity of the polypeptide can be determined by analyzing the imidazolinone resistance of a plant expressing the polypeptide as described in the Examples below.

To determine the percent sequence identity of two amino acid sequences, the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings.

It is to be understood that for the purposes of determining sequence identity, when comparing a DNA sequence to an RNA sequence, a thymidine nucleotide is equivalent to a uracil nucleotide. Preferably, the isolated IMI polypeptides included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2 or SEQ ID NO:4. In another embodiment, the isolated MI polypeptides included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2 or SEQ ID NO:4.

Additionally, optimized IMI nucleic acids can be created. Preferably, an optimized IMI nucleic acid encodes an IMI polypeptide that modulates a plant's tolerance to imidazolinone herbicides, and more preferably increases a plant's tolerance to an imidazolinone herbicide upon its overexpression in the plant. As used herein, "optimized" refers to a nucleic acid that is genetically engineered to increase its expression in a given plant or animal. To provide plant optimized IMI nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) eliminate sequences that cause destabilization, inappropriate polyadenylation, degradation and termination of RNA, or that form secondary structure hairpins or RNA splice sites. Increased expression of IMI nucleic acids in plants can be achieved by utilizing the distribution frequency of codon usage in plants in general or a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, Proc. Natl. Acad. Sci. USA 88:3324-3328; and Murray et al., 1989, Nucleic Acids Res. 17:477-498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A=n=1 \ Z \ X_n-Y_nX_n$ times $100 \ Z$ where $X_n$=frequency of usage for codon n in the host cell; $Y_n$=frequency of usage for codon n in the synthetic gene, n represents an individual codon that specifies an amino acid and the total number of codons is Z. The overall deviation of the frequency of codon usage, A, for all amino acids should preferably be less than about 25%, and more preferably less than about 10%.

Hence, an IMI nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized IMI nucleic acids of this invention also preferably have CG and TA doublet avoidance indices closely approximating those of the chosen host plant (i.e., *Triticum aestivum*). More preferably these indices deviate from that of the host by no more than about 10-15%.

In addition to the nucleic acid molecules encoding the IMI polypeptides described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation and/or stability of the target polynucleotide. Methods are described in the prior art for targeting the antisense polynucleotide to the chromosomal DNA, to a primary RNA transcript or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide sequence of SEQ ID NO:2 or SEQ ID NO:4.

In addition to the IMI nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of the sequence set forth in SEQ ID NO:1 or SEQ ID NO:3, an anti-sense sequence of the sequence set forth in SEQ ID NO:1 or SEQ ID NO:3, or naturally occurring mutants thereof. Primers based on a nucleotide sequence of SEQ ID NO:1 or SEQ ID NO:3 can be used in PCR reactions to clone IMI homologs. Probes based on the IMI nucleotide sequences can be used to detect transcripts or genomic sequences encoding the same or homologous polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an IMI polypeptide, such as by measuring a level of an IMI-encoding nucleic acid, in a sample of cells, e.g., detecting IMI mRNA levels or determining whether a genomic IMI gene has been mutated or deleted.

The invention further provides an isolated recombinant expression vector comprising an IMI nucleic acid as described above, wherein expression of the vector in a host cell results in increased resistance to an imidazolinone herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. With respect to a recombinant expression vector, "operatively linked" is intended to mean that the nucleotide sequence of interest is linked to the regulatory sequence(s) in a manner which allows for expression of the nucleotide sequence (e.g., in an iii vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., IMI polypeptides, fusion polypeptides, etc.).

In a preferred embodiment of the present invention, the IMI polypeptides are expressed in plants and plants cells such as unicellular plant cells (such as algae) (See Falciatore et al., 1999, Marine Biotechnology 1(3):239-251 and references therein) and plant cells from higher plants (e.g., the spermatophytes, such as crop plants). An IMI polynucleotide may be "introduced" into a plant cell by any means, including transfection, transformation or transduction, electroporation, particle bombardment, agroinfection, biolistics and the like.

Suitable methods for transforming or transfecting host cells including plant cells can be found in Sambrook et al. (Molecular Cloning: A Laboratory Manual. $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As increased resistance to imidazolinone herbicides is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses and forage crops, these crop plants are also preferred target plants for a genetic engineering as one further embodiment of the present invention. In a preferred embodiment, the plant is a wheat plant Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of an IMI polynucleotide into a plant is achieved by *Agrobacterium* mediated gene transfer. One transformation method known to those of skill in the art is the dipping of a flowering plant into an Agrobacteria solution, wherein the Agrobacteria contains the IMI nucleic acid, followed by breeding of the transformed gametes. *Agrobacterium* mediated plant transformation can be performed using for example the GV3 101 (MP90) (Koncz and Schell, 1986, Mol. Gen. Genet. 204:383-396) or LBA-4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, $2^{nd}$ Ed.—Dordrecht: Kluwer Academic Publ., 1995,—in Sect., Ringbuc Zentrale Signatur: BT11-P ISBN 0-7923-27314; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced IMI polynucleotide may be maintained in the plant cell stably if it is incorporated into a non-chromosomal autonomous replicon or integrated into the plant chromosomes. Alternatively, the introduced IMI polynucleotide may be present on an extra-chromosomal non-replicating vector and be transiently expressed or transiently active. In one embodiment, a homologous recombinant microorganism can be created wherein the IMI polynucleotide is integrated into a chromosome, a vector is prepared which contains at least a portion of an AHAS gene into which a deletion, addition or substitution has been introduced to thereby alter, e.g., functionally disrupt, the endogenous AHAS gene and to create an IMI gene. To create a point mutation via homologous recombination, DNA-RNA hybrids can be used in a technique known as chimeraplasty (Cole-Strauss et al., 1999, Nucleic Acids Research 27(5):1323-1330 and Kmiec, 1999, Gene therapy American Scientist 87(3):240-247). Other homologous recombination procedures in *Triticum* species are also well known in the art and are contemplated for use herein.

In the homologous recombination vector, the IMI gene can be flanked at its 5' and 3' ends by an additional nucleic acid molecule of the AHAS gene to allow for homologous recombination to occur between the exogenous IMI gene carried by the vector and an endogenous AHAS gene, in a microorganism or plant. The additional flanking AHAS nucleic acid molecule is of sufficient length for successful homologous recombination with the endogenous gene. Typically, several hundreds of base pairs up to kilobases of flanking DNA (both at the 5' and 3' ends) are included in the vector (See, e.g., Thomas, K. R., and Capecchi, M. R., 1987, Cell 51:503 for a description of homologous recombination vectors or Strepp et al., 1998, PNAS, 95(8):4368-4373 for cDNA based recombination in *Physcomitrella patens*). However, since the IMI gene normally differs from the AHAS gene at very few amino acids, a flanking sequence is not always necessary. The homologous recombination vector is introduced into a microorganism or plant cell (e.g., via polyethylene glycol mediated DNA), and cells in which the introduced IMI gene has homologously recombined with the endogenous AHAS gene are selected using art-known techniques.

In another embodiment, recombinant microorganisms can be produced that contain selected systems that allow for regulated expression of the introduced gene. For example, inclusion of an IMI gene on a vector placing it under control of the lac operon permits expression of the IMI gene only in the presence of IPTG. Such regulatory systems are well known in the art Whether present in an extra-chromosomal non-replicating vector or a vector that is integrated into a chromosome, the IMI polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operatively linked to an appropriate promoter conferring gene expression in a timely, cell type-preferred, or tissue-preferred manner. Promoters useful in the expression cassettes of the invention include any promoter that is capable of initiating transcription in a plant cell. Such promoters include, but are not limited to those that can be obtained from plants, plant viruses and bacteria that contain genes that are expressed in plants, such as *Agrobacterium* and *Rhizobium*.

The promoter may be constitutive, inducible, developmental stage-preferred, cell type-preferred, tissue-preferred or organ-preferred. Constitutive promoters are active under most conditions. Examples of constitutive promoters include the CaMV 19S and 35S promoters (Odell et al., 1985, Nature 313:810-812), the sX CaMV 35S promoter (Kay et al., 1987, Science 236:1299-1302) the Sep1 promoter, the rice actin promoter (McElroy et al., 1990, Plant Cell 2:163-171), the *Arabidopsis* actin promoter, the ubiquitan promoter (Christensen et al., 1989, Plant Molec. Biol. 18:675-689); pEmu (Last et al., 1991, Theor. Appl. Genet 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89-108). Chemically inducible promoters are especially suitable if time-specific gene expression is desired. Examples of such promoters are a salicylic acid inducible promoter (PCT Application No. WO 95/19443), a tetracycline inducible promoter (Gatz et al., 1992, Plant J. 2:397-404) and an ethanol inducible promoter (PCT Application No. WO 93/21334).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters and the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol Gen Genet 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15kD zein promoter, the 22kD zein promoter, the 27kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729-736).

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an IMI polynucleotide can be expressed in bacterial cells such as C. glutanmicum, insect cells, fungal cells, or mammalian cells (such as Chinese hamster ovary cells (CHO) or COS cells), algae, ciliates, plant cells, fungi or other microorganisms like C. glutamicum. Other suitable host cells are known to those skilled in the art.

A host cell of the invention, such as a prokaryotic or eukaryotic host cell in culture, can be used to produce (i.e., express) an IMI polynucleotide. Accordingly, the invention further provides methods for producing IMI polypeptides using the host cells of the invention. In one embodiment, the method comprises culturing the host cell of invention (into which a recombinant expression vector encoding an IMI polypeptide has been introduced, or into which genome has been introduced a gene encoding a wild-type or IMI polypeptide) in a suitable medium until IMI polypeptide is produced. In another embodiment, the method further comprises isolating IMI polypeptides from the medium or the host cell. Another aspect of the invention pertains to isolated IMI polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of IMI polypeptide in which the polypeptide is separated from some of the cellular components of the cells in which it is naturally or recombinantly produced. In one embodiment, the language "substantially free of cellular material" includes preparations of an ING polypeptide having less than about 30% (by dry weight) of non-IMI material (also referred to herein as a "contaminating polypeptide"), more preferably less than about 20% of non-IMI material, still more preferably less than about 10% of non-IMI material, and most preferably less than about 5% non-IMI material.

When the IMI polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of IMI polypeptide in which the polypeptide is separated from chemical precursors or other chemicals that are involved in the synthesis of the polypeptide. In one embodiment, the language "substantially free of chemical precursors or other chemicals" includes preparations of an IMI polypeptide having less than about 30% (by dry weight) of chemical precursors or non-IMI chemicals, more preferably less than about 20% chemical precursors or non-IMI chemicals, still more preferably less than about 10% chemical precursors or non-IMI chemicals, and most preferably less than about 5% chemical precursors or non-IMI chemicals. In preferred embodiments, isolated polypeptides, or biologically active portions thereof, lack contaminating polypeptides from the same organism from which the IMI polypeptide is derived. Typically, such polypeptides are produced by recombinant expression of, for example, a *Triticum aestivum* IMI polypeptide in plants other than *Triticum aestivum* or microorganisms such as C. glutamicum, ciliates, algae, or fungi.

The IMI polynucleotide and polypeptide sequences of the invention have a variety of uses. The nucleic acid and amino acid sequences of the present invention can be used to transform plants, thereby modulating the plant's resistance to imidazolinone herbicides. Accordingly, the invention provides a method of producing a transgenic plant having increased tolerance to an imidazolinone herbicide comprising, (a) transforming a plant cell with one or more expression vectors comprising one or more IMI nucleic acids, and (b) generating from the plant cell a transgenic plant with an increased resistance to an imidazolinone herbicide as compared to a wild type variety of the plant In one embodiment, the multiple IMI nucleic acids are derived from different genomes. Also included in the present invention are methods of producing a transgenic plant having increased tolerance to an imidazolinone herbicide comprising, (a) transforming a plant cell with an expression vector comprising an IMI nucleic acid, wherein the nucleic acid is a non-Imi1 nucleic acid and (b) generating from the plant cell a transgenic plant with an increased resistance to an imidazolinone herbicide as compared to a wild type variety of the plant.

The present invention includes methods of modifying a plant's tolerance to an imidazolinone herbicide comprising modifying the expression of one or more IMI nucleic acids. Preferably, the nucleic acids are located on or derived from different genomes. The plant's resistance to the imidazolinone herbicide can be increased or decreased as achieved by increasing or decreasing the expression of an IMI polynucleotide, respectively. Preferably, the plant's resistance to the imidazolinone herbicide is increased by increasing expression of an IMI polynucleotide. Expression of an IMI polynucleotide can be modified by any method known to those of skill in the art. The methods of increasing expression of IMI polynucleotides can be used wherein the plant is either transgenic or not transgenic. In cases when the plant is transgenic, the plant can be transformed with a vector containing any of the above described MI coding nucleic acids, or the plant can be transformed with a promoter that directs expression of endogenous IMI polynucleotides in the plant, for example. The invention provides that such a promoter can be tissue specific or developmentally regulated. Alternatively, non-transgenic plants can have endogenous IMI polynucleotide expression modified by inducing a native promoter. The expression of polynucleotides comprising a polynucleotide sequence as defined in SEQ ID NO:1 or SEQ ID NO:3 in target plants can be accomplished by, but is not limited to, one of the following examples: (a) constitutive promoter, (b) chemical-induced promoter, and (c) engineered promoter over-expression with for example zinc-finger derived transcription factors (Greisman and Pabo, 1997, Science 275: 657).

In a preferred embodiment, transcription of the IMI polynucleotide is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as an IMI nucleic acid. Therefore, activating and repressing ZFPs can be created that specifically recognize the IMI polynucleotide promoters described above and used to increase or decrease IMI polynucleotide expression in a plant, thereby modulating the herbicide resistance of the plant.

As described in more detail above, the plants produced by the methods of the present invention can be monocots or dicots. The plants can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and forage crops, for example. In a preferred embodiment, the plant is a wheat plant or triticale plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover. In a preferred embodiment, the plant is a wheat plant. In each of the methods described above, the plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations.

As described above, the present invention teaches compositions and methods for increasing the imidazolinone resistance of a wheat plant or seed as compared to a wild-type variety of the plant or seed. In a preferred embodiment, the imidazolinone resistance of a wheat plant or seed is increased such that the plant or seed can withstand an imidazolinone herbicide application of preferably approximately 10400 g ai ha$^{-1}$, more preferably 20-160 g ai ha$^{-1}$, and most preferably 40-80 g ai ha$^{-1}$. As used herein, to "withstand" an imidazolinone herbicide application means that the plant is either not killed or not injured by such application.

Additionally provided herein is a method of controlling weeds within the vicinity of a wheat or triticale plant, comprising applying an imidazolinone herbicide to the weeds and to the wheat or triticale plant, wherein the wheat or triticale plant has increased resistance to the imidazolinone herbicide as compared to a wild type variety of the wheat or triticale plant, and wherein the imidazolinone resistant wheat or triticale plant comprises at least one IMI nucleic acid. In one embodiment, the plant comprises multiple IMI nucleic acids located on or derived from different genomes, wherein the at least one IMI nucleic acid is selected from the group consisting of an Imi1 nucleic acid, an Imi2 nucleic acid, and an Imi3 nucleic acid. In another embodiment, the plant comprises an Imi1 nucleic acid and an Imi3 nucleic acid. By providing for wheat and triticale plants having increased resistance to imidazolinone, a wide variety of formulations can be employed for protecting wheat and triticale plants from weeds, so as to enhance plant growth and reduce competition for nutrients. An imidazolinone herbicide can be used by itself for pre-emergence, post-emergence, pre-planting, and at-planting control of weeds in areas surrounding the wheat plants described herein or an imidazolinone herbicide formulation can be used that contains other additives. The imidazolinone herbicide can also be used as a seed treatment. Additives found in an imidazolinone herbicide formulation include other herbicides, detergents, adjuvants, spreading agents, sticking agents, stabilizing agents, or the like. The imidazolinone herbicide formulation can be a wet or dry preparation and can include, but is not limited to, flowable powders, emulsifiable concentrates and liquid concentrates. The imidazolinone herbicide and herbicide formulations can be applied in accordance with conventional methods, for example, by spraying, irrigation, dusting, or the like.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Mutagenesis and Selection of Resistant Wheat Lines 840 grams of seed of the *Triticum aestivum* wheat varieties Krichauff and Brookton were soaked in a sodium azide solution (0.065 g/L) to produce M1 seed. M1 plants were allowed to self pollinate to produce M2 seed. M2 seed were soaked in a 50 ppm solution of the imidazolinone herbicide imazamox for 24 hours prior to sowing in the field. Resultant plants that appeared to have normal growth eight to nine weeks after sowing were transplanted from the field to a greenhouse for M3 seed production. To confirm herbicide tolerance, M3 seed were soaked in a 50 ppm solution of imazanmox for 24 hours prior to sowing, and subsequent plants were sprayed with a solution of 50 ppm of imazamox. The M2-derived line of Krichauff designated K-42 and the M2-derived line of Brookton designated Br-8 were identified as tolerant to imazamox.

The tolerance to imazamox in K-42 and Br-8 segregated as expected for a trait controlled by a semi-dominant gene. FS-2 is a bread wheat line with a mutation in the Als1 AHAS gene that confers tolerance to imidazolinone herbicides such as imazamox. Evaluation of the F2 generation from a cross of K-42 and FS-2, from a cross of K-42 and Br-8, and from a cross of Br-8 and FS-2 suggested that K-42 was non-allelic to both FS-2 and Br-8, and that FS-2 and Br-8 were allelic with respect to herbicide tolerance. Subsequent molecular characterization revealed K-42 to have a mutation in the Als3 AHAS gene and Br-8 to have a mutation in the Als1 AHAS gene, each conferring tolerance to imidazolinone herbicides.

Example 2

Tolerance to IMI Herbicides Provided by K-42 and Br-8

Tolerance of K-42 and Br-8 to the imidazolinone herbicide imazamox was evaluated at 40 and 120 g/ha in the greenhouse. Wild type Krichauff and Brookton were used as herbicide susceptible controls. 24 plants were treated at each rate at the 2-3 leaf stage. Injury was scored on a 0-9 scale, 0 representing no injury and 9 representing plant death. FIG. 4 summarizes the data collected 14 and 21 days after treatment.

Because the tolerance in K-42 and Br-8 is due to a mutation in the AHAS enzyme rendering it resistant to inhibition by imidazolinone herbicides, the in vitro activity of AHAS extracted from wild type plants (not having the mutation for tolerance) can be compared to the in vitro activity of AHAS extracted from tolerant plants in the presence of varying concentrations of an imidazolinone herbicide. K-142 was compared to the wild type variety Krichauff, and Br-8 was compared to the wild type variety Brookton. The results are presented in FIG. 5. As the concentration of imazamox increased, the uninhibited AHAS enzyme activity decreased faster in wild type lines than in either Br-8 or K-42. At 100 HM imazamox, the residual uninhibited AHAS is sufficient to provide a herbicide tolerant response both Br-8 and K-42.

Example 3

Increased Tolerance to IMI Herbicides Provided by Combining Imi-Tolerant Mutations in Als1 and Als3

In Example 1, reference was made to crosses between K-42, containing a mutation in Als3 conferring imidazolinone herbicide tolerance, and FS-2 and Br-8, each containing a mutation in Als1 also conferring imidazolinone herbicide tolerance. Krichauff and Brookton are the wheat varieties from which K-42 and Br-8, respectively, were derived. Lines derived from the K-42/FS-2 cross were tolerant to rates of up to six times that required for economic weed control in the field. One line derived from the K-42/Br-8 cross was evaluated in the greenhouse for tolerance to 40 and 120 grams/hectare of imazamox. Injury was scored on a 0-9 scale, 0 representing no injury and 9 representing plant death. As shown in FIG. 6, the data clearly show the combination of K-42 and Br-8 non-allelic tolerance genes confer greatly enhanced tolerance at both 40 and 120 g/ha with very little injury.

As explained in Example 2, the in vitro AHAS enzyme activity can be compared among lines with and without a mutation conferring resistance to inhibition by imidazolinone herbicides. The same lines described above in the greenhouse tolerance experiment were evaluated with respect to percent uninhibited AHAS enzyme activity using the imidazolinone herbicide imazethapyr. The data are presented in FIG. 7. The increased tolerance seen in the Br-8/K-42 combination in greenhouse studies is mirrored by the increase in percent uninhibited AHAS activity seen in this combination at the four highest herbicide concentrations.

We claim

1. A seed of wheat line Krichauff IMI K-42, representative seed of said line having been deposited under ATCC Patent Deposit Designation Number PTA-4257.

2. A wheat plant, or a part thereof, produced by growing a seed of wheat line Krichauff IMI K-42, representative seed of said line having been deposited under ATCC Patent Deposit Designation Number PTA-4257.

3. A method for producing a hybrid wheat seed wherein the method comprises crossing a first wheat plant with a different wheat plant and harvesting the resulting hybrid wheat seed, wherein the first wheat plant is produced by growing a seed of wheat line Krichauff IMI K-42, representative seed of said line having been deposited under ATCC Patent Deposit Designation Number PTA-4257.

4. A hybrid wheat seed produced by a method comprising crossing a first wheat plant with a different wheat pant and harvesting the resulting hybrid wheat seed, wherein the first wheat plant is produced by growing a seed of wheat line Krichauff IMI K-42, representative seed of said line having been deposited under ATCC Patent Deposit Designation Number PTA-4257.

5. A wheat plant, or a part thereof, produced by growing a hybrid wheat seed produced by a method comprising crossing a first wheat plant with a different wheat plant and harvesting the resulting hybrid wheat seed, wherein the first wheat plant is produced by growing a seed of wheat line Krichauff IMI K-42, representative seed of said line having been deposited under ATCC Patent Deposit Designation Number PTA-4257.

* * * * *

```
                         SEQUENCE LISTING

<160> NUMBER OF SEQ ID NOS: 9

<210> SEQ ID NO 1
<211> LENGTH: 509
<212> TYPE: DNA
<213> ORGANISM: Triticum aestivum

<400> SEQUENCE: 1
cggctcagta ttcacttac  aagcggccac ggcagtggct gtcttcgtct ggtttggggg     60
caatgggatt tgggttacca gctgcagctg gcgctgctgt ggccaaccca ggtgttacag    120
ttgttgacat tgatggtgat ggtagtttcc tcatgaacat tcaggagttg gcgttgatcc    180
gcattgagaa cctcccagtg aaggtgatga tattgaacaa ccagcatctg ggaatggtgg    240
tgcagtggga ggataggttt tacaaggcca atcgggcgca cacataccct ggcaacccag    300
aaaatgagag tgagatatat ccagattttg tgacgattgc taaaggattc aacgttccag    360
cagttcgagt gacgaagaag agcgaagtca ctgcagcaat caagaagatg cttgagaccc    420
cagggccata cttgttggat atcatagtcc cgcatcagga gcacgtgctg cctatgatcc    480
caaacggtgg tgctttcaag gacatgatc                                      509

<210> SEQ ID NO 2
<211> LENGTH: 169
<212> TYPE: PRT
<213> ORGANISM: Triticum aestivum

<400> SEQUENCE: 2

Ala Gln Tyr Tyr Thr Tyr Lys Arg Pro Arg Gln Trp Leu Ser Ser Ser
 1               5                  10                  15

Gly Leu Gly Ala Met Gly Phe Gly Leu Pro Ala Ala Ala Gly Ala Ala
             20                  25                  30

Val Ala Asn Pro Gly Val Thr Val Val Asp Ile Asp Gly Asp Gly Ser
         35                  40                  45

Phe Leu Met Asn Ile Gln Glu Leu Ala Leu Ile Arg Ile Glu Asn Leu
     50                  55                  60
```

```
Pro Val Lys Val Met Ile Leu Asn Asn Gln His Leu Gly Met Val Val
 65                  70                  75                  80

Gln Trp Glu Asp Arg Phe Tyr Lys Ala Asn Arg Ala His Thr Tyr Leu
                 85                  90                  95

Gly Asn Pro Glu Asn Glu Ser Glu Ile Tyr Pro Asp Phe Val Thr Ile
            100                 105                 110

Ala Lys Gly Phe Asn Val Pro Ala Val Arg Val Thr Lys Lys Ser Glu
        115                 120                 125

Val Thr Ala Ala Ile Lys Lys Met Leu Glu Thr Pro Gly Pro Tyr Leu
130                 135                 140

Leu Asp Ile Ile Val Pro His Gln Glu His Val Leu Pro Met Ile Pro
145                 150                 155                 160

Asn Gly Gly Ala Phe Lys Asp Met Ile
                165
```

<210> SEQ ID NO 3
<211> LENGTH: 575
<212> TYPE: DNA
<213> ORGANISM: Triticum aestivum

<400> SEQUENCE: 3

```
gcggctcagt attacactta caagcggcca cggcagtggc tgtcttcgtc tggtttgggg      60
gcaatgggat ttgggttacc agctgcagct ggcgctgctg tggccaaccc aggtgttaca     120
gttgttgaca ttgatggaga tggtagtttc ctcatgaaca ttcaggagtt ggcattgatc     180
cgtattgaga acctccctgt gaaggtgatg atattgaaca accagcatct gggaatggtg     240
gtgcaatggg aggataggtt ttacaaggcc aatcgggcgc acacatacct tggcaaccca     300
gaaaatgaga gtgagatata tccagatttt gtgacgattg ctaaaggatt caacgttccg     360
gcagttcgtg tgacgaagaa gagcgaagtc actgcagcaa tcaagaagat gcttgagacc     420
ccagggccat acttgttgga tatcatcgtc ccgcatcagg agcacgtgct gcctatgatc     480
ccaaacggtg gtgctttcaa ggacatgatc atggagggtg atggcaggac ctcgtactga     540
aatttcgacc tacaagacct acaagtgtga catgc                                575
```

<210> SEQ ID NO 4
<211> LENGTH: 170
<212> TYPE: PRT
<213> ORGANISM: Triticum aestivum

<400> SEQUENCE: 4

```
Ala Ala Gln Tyr Tyr Thr Tyr Lys Arg Pro Arg Gln Trp Leu Ser Ser
  1               5                  10                  15

Ser Gly Leu Gly Ala Met Gly Phe Gly Leu Pro Ala Ala Ala Gly Ala
             20                  25                  30

Ala Val Ala Asn Pro Gly Val Thr Val Val Asp Ile Asp Gly Asp Gly
         35                  40                  45

Ser Phe Leu Met Asn Ile Gln Glu Leu Ala Leu Ile Arg Ile Glu Asn
     50                  55                  60

Leu Pro Val Lys Val Met Ile Leu Asn Asn Gln His Leu Gly Met Val
 65                  70                  75                  80

Val Gln Trp Glu Asp Arg Phe Tyr Lys Ala Asn Arg Ala His Thr Tyr
                 85                  90                  95

Leu Gly Asn Pro Glu Asn Glu Ser Glu Ile Tyr Pro Asp Phe Val Thr
            100                 105                 110
```

```
Ile Ala Lys Gly Phe Asn Val Pro Ala Val Arg Val Thr Lys Lys Ser
        115                 120                 125

Glu Val Thr Ala Ala Ile Lys Lys Met Leu Glu Thr Pro Gly Pro Tyr
130                 135                 140

Leu Leu Asp Ile Ile Val Pro His Gln Glu His Val Leu Pro Met Ile
145                 150                 155                 160

Pro Asn Gly Gly Ala Phe Lys Asp Met Ile
                165                 170

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 5

Ala Ile Thr Gly Gln Val Pro Arg Arg Met Ile Gly Thr
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 6

Gln Trp Glu Asp
1

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 7

Val Phe Ala Tyr Pro Gly Gly Ala Ser Met Glu Ile His Gln Ala Leu
1               5                   10                  15

Thr Arg Ser

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:
      Illustrative conserved peptide sequence

<400> SEQUENCE: 8

Ala Phe Gln Glu Thr Pro
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:
      Illustrative conserved peptide sequence
```

-continued

```
<400> SEQUENCE: 9

Ile Pro Ser Gly Gly
 1               5
```